US009676805B2

(12) United States Patent
Dyballa et al.

(10) Patent No.: US 9,676,805 B2
(45) Date of Patent: Jun. 13, 2017

(54) PURIFYING ORGANOPHOSPHORUS COMPOUNDS CONTAMINATED WITH CHLORINE

(71) Applicant: Evonik Degussa GmbH, Essen (DE)

(72) Inventors: Katrin Marie Dyballa, Recklinghausen (DE); Robert Franke, Marl (DE); Dirk Fridag, Haltern am See (DE); Markus Priske, Mobile, AL (US)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 15/109,745

(22) PCT Filed: Jan. 16, 2015

(86) PCT No.: PCT/EP2015/050778
§ 371 (c)(1),
(2) Date: Jul. 5, 2016

(87) PCT Pub. No.: WO2015/113840
PCT Pub. Date: Aug. 6, 2015

(65) Prior Publication Data
US 2016/0326197 A1  Nov. 10, 2016

(30) Foreign Application Priority Data
Jan. 31, 2014 (DE) .................. 10 2014 201 756

(51) Int. Cl.
C07F 9/6574 (2006.01)
C07C 45/00 (2006.01)
C07C 253/00 (2006.01)
B01J 31/18 (2006.01)
C07C 5/02 (2006.01)

(52) U.S. Cl.
CPC ......... *C07F 9/65746* (2013.01); *B01J 31/185* (2013.01); *C07C 5/02* (2013.01); *C07C 45/00* (2013.01); *C07C 253/00* (2013.01); *B01J 2231/321* (2013.01); *B01J 2231/322* (2013.01); *B01J 2231/645* (2013.01); *C07C 2531/22* (2013.01)

(58) Field of Classification Search
CPC ..................... C07F 9/65746; B01J 31/185
See application file for complete search history.

(56) References Cited

U.S. PATENT DOCUMENTS

| | | |
|---|---|---|
| 6,350,819 B1 | 2/2002 | Tulchinsky et al. |
| 6,469,145 B1 * | 10/2002 | Rastogi ............... C12N 9/16 424/94.1 |
| 6,472,550 B1 | 10/2002 | Toan et al. |
| 7,345,185 B2 | 3/2008 | Ortmann et al. |
| 7,767,861 B2 | 8/2010 | Ortmann et al. |
| 8,003,816 B2 | 8/2011 | Selent et al. |
| 8,609,878 B2 | 12/2013 | Fridag et al. |
| 8,729,287 B2 | 5/2014 | Fridag et al. |
| 9,000,220 B2 | 4/2015 | Christiansen et al. |
| 9,127,030 B2 | 9/2015 | Kreidler et al. |
| 9,206,105 B2 | 12/2015 | Christiansen et al. |
| 9,212,195 B1 | 12/2015 | Dyballa et al. |
| 9,217,003 B2 | 12/2015 | Dyballa et al. |
| 9,221,850 B2 | 12/2015 | Dyballa et al. |
| 9,221,851 B2 | 12/2015 | Dyballa et al. |
| 9,272,973 B2 | 3/2016 | Fridag et al. |
| 2008/0076944 A1 | 3/2008 | Bartsch et al. |
| 2013/0317246 A1 | 11/2013 | Kreidler et al. |
| 2014/0206904 A1 | 7/2014 | Fridag et al. |
| 2014/0309423 A1 | 10/2014 | Christiansen et al. |
| 2015/0011132 A1 | 1/2015 | Shibuya et al. |
| 2015/0011139 A1 | 1/2015 | Anneaux et al. |
| 2015/0266008 A1 | 9/2015 | Christiansen et al. |
| 2015/0273455 A1 | 10/2015 | Christiansen et al. |
| 2015/0290633 A1 | 10/2015 | Christiansen et al. |
| 2015/0336093 A1 | 11/2015 | Dyballa et al. |
| 2015/0336861 A1 | 11/2015 | Geilen et al. |
| 2015/0336865 A1 | 11/2015 | Dyballa et al. |
| 2015/0336885 A1 | 11/2015 | Dyballa et al. |

(Continued)

FOREIGN PATENT DOCUMENTS

CN 101684130 A 3/2010
DE 60001533 T2 10/2003

(Continued)

OTHER PUBLICATIONS

Dyballa et al., U.S. Appl. No. 15/058,426, filed Mar. 2, 2016.

(Continued)

*Primary Examiner* — Golam M M Shameem
(74) *Attorney, Agent, or Firm* — Philip P. McCann; Smith Moore Leatherwood LLP

(57) ABSTRACT

The invention relates to a process for the purification of a contaminated organophosphorus product which comprises at least one organophosphorus compound and, as contaminant, at least one chlorine compound. It is based on the object of indicating a purification method in which the chlorine content of an organophosphorus product which comprises at least one organophosphorus compound and at least one chlorine compound as contaminant, can be reduced from originally 1000 to 100 000 ppm to a total chlorine content between 10 ppm and 10 000 ppm. This is achieved by a process with the steps:

a) provision of the contaminated organophosphorus product;

b) complete dissolution of the contaminated organophosphorus product in a solvent to give a contaminated solution;

c) separation of the contaminated solution by means of a filter and/or by means of a membrane separation unit to give a purified solution;

d) removal of the solvent from the purified solution to give a purified organophosphorus product.

15 Claims, No Drawings

(56) References Cited

U.S. PATENT DOCUMENTS

| | | |
|---|---|---|
| 2015/0336995 A1 | 11/2015 | Dyballa et al. |
| 2016/0010225 A1 | 1/2016 | Dyballa et al. |
| 2016/0010226 A1 | 1/2016 | Dyballa et al. |
| 2016/0017504 A1 | 1/2016 | Dyballa et al. |
| 2016/0017505 A1 | 1/2016 | Dyballa et al. |

FOREIGN PATENT DOCUMENTS

| | | |
|---|---|---|
| DE | 102004049339 A1 | 4/2006 |
| DE | 102006058682 A1 | 6/2008 |
| DE | 102013219506 A1 | 4/2014 |
| DE | 102013219508 A1 | 4/2014 |
| EP | 0285136 A2 | 10/1988 |
| EP | 1097936 A1 | 5/2001 |
| EP | 1097936 B1 | 3/2003 |
| EP | 2003138 A1 | 12/2008 |
| EP | 2091958 B1 | 4/2011 |
| WO | 0121627 A1 | 3/2001 |
| WO | 2012095253 A1 | 7/2012 |
| WO | 2012095255 A1 | 7/2012 |
| WO | 2014056735 A1 | 4/2014 |
| WO | 2014177355 A1 | 11/2014 |
| WO | 2015176927 A1 | 6/2015 |
| WO | 2015121007 A1 | 8/2015 |
| WO | 2015176929 A1 | 11/2015 |
| WO | 2015181018 A1 | 12/2015 |

OTHER PUBLICATIONS

English language International Search Report mailed on May 4, 2015 in PCT/EP2015/050778 (3 pages).

Geilen et al., U.S. Appl. No. 15/040,058, filed Feb. 10, 2016.

German language International Search Report mailed on May 4, 2015 in PCT/EP2015/050778 (4 pages).

German language Search Report mailed on Sep. 3, 2014 in DE 10 2014 201 756.4 (8 pages).

German language Written Opinion mailed on May 4, 2015 in PCT/EP2015/050778 (6 pages).

* cited by examiner

PURIFYING ORGANOPHOSPHORUS COMPOUNDS CONTAMINATED WITH CHLORINE

This application is a national stage application under 35 U.S.C. §371 of International Application No. PCT/EP2015/050778 filed 16 Jan. 2015, which claims priority to German Application No. 10 2014 201 756.4 filed 31 Jan. 2014, the disclosures of which are expressly incorporated herein by reference.

FIELD

The invention relates to a process for the purification of a contaminated organophosphorus product which comprises at least one organophosphorus compound and, as contaminant, at least one chlorine compound. Furthermore, the invention relates to a process for producing a catalyst system, in the course of which a contaminated organophosphorus product is purified, and also to a process for hydroformylation or for the hydrocyanation or for the hydrogenation of unsaturated compounds in the presence of a homogeneous catalyst system whose ligand has been purified in this way.

BACKGROUND

Organophosphorus compounds are chemical compounds which comprise primarily the elements carbon, hydrogen and phosphorus. Optionally they also comprise oxygen and nitrogen. In addition, the organophosphorus compounds can comprise further elements such as halogens, sulfur etc. in the form of substituents. The term here includes both those organophosphorus compounds which have a P—C bond, as well as those without P—C bond, i.e. with a P—O or a P—N bond.

Organophosphorus compounds have gained considerable industrial significance because of their wide range of use. They are used directly as plasticizers, flame retardants, UV stabilizers or as antioxidants. In addition, they are important intermediates in the production of fungicides, herbicides, insecticides and pharmaceuticals.

A specific field of use of the organophosphorus compounds is catalysis:

For instance, especially phosphines, phosphites and phosphoramidites are used as ligands in catalyst complexes, which are used in turn for the homogeneous catalysis of processes operated on an industrial scale. Particular mention should be made of the hydroformylation of unsaturated compounds with carbon monoxide and hydrogen, which generally takes place in the presence of a homogeneous catalyst system which has a metal and at least one organophosphorus compound as ligand. An introduction to homogeneously catalysed hydroformylation is given in:

B. CORNILS, W. A. HERRMANN: Applied Homogeneous Catalysis with Organometallic Compounds. Vol. 1 & 2, VCH, Weinheim, N.Y., 1996

R. Franke, D. Selent, A. Börner: Applied Hydroformylation. Chem. Rev., 2012, DOI:10.1021/cr3001803

The synthesis of phosphorus ligands is described repeatedly in the literature. A good overview can be found in "Phosphorous(III) Ligands in Homogeneous Catalysis—Design and Synthesis" by Paul C. J. Kamer and Piet W. N. M. van Leeuwen; John Wiley and Sons, 2012.

In the synthesis of these ligands, chlorine-containing reagents are frequently used. For instance, in the synthesis of phosphite ligands, phosphorus trichloride ($PCl_3$) is usually used.

The chlorine compounds used in the preparation of organophosphorus compounds present many difficulties in the proper use or further processing of the organophosphorus compound:

For instance, the desired organophosphorus compound is never obtained in pure form immediately, and is always obtained in contaminated form as an organophosphorus product which, as well as the desired organophosphorus compound, also contains contaminants. The contaminants are unconverted or incompletely converted reagents, auxiliaries or products from side reactions. In this context, contaminants in the form of chlorine compounds present particular difficulties:

If the chlorine-containing contaminants get into a steel pressure reactor together with the organophosphorus compound used as ligand, the pressure reactor is subject to increased corrosion as a result of the chloride. This is especially true of continuous processes, in which the organophosphorus compounds are metered in over the course of the reaction. This is the case, for example, when the organophosphorus compound is used as a ligand in industrial scale hydroformylation. The metered addition inevitably also results in an accumulation of the secondary components in the reactor. This is particularly critical if chloride is one of the secondary components since chloride attacks even stainless steels:

Merkblatt [Information sheet] 893 "Edelstahl rostfrei für die Wasserwirtschaft" [Corrosion-free stainless steel for water management], 1st edition 2007, publisher: Informationsstelle Edelstahl Rostfrei, Dusseldorf.

In the presence of chloride ions, there is a particular risk of stress-cracking corrosion, which can lead in more favourable cases to a premature shutdown of the process and to a reactor overhaul, but in less favourable cases even to rupture of the reactor. It is therefore of overriding importance to prevent entrainment of chlorine-containing compounds via the organophosphorus catalyst system.

The ready-to-use phosphorus ligands should contain less than 10 000 ppm, better still less than 1 000 ppm total chlorine. For a total chlorine content in this order of magnitude, the risk of stress-cracking corrosion in the reactor can be controlled in industrially implemented processes. Although the aforementioned leaflet considers a chlorine content of 200 ppm to be critical, in industrial chemical processes the organophosphorus compound is only used in catalytic amounts, meaning that the total chlorine content in the reactor is, on account of dilution by the reactants, significantly less than 200 ppm, if the degree of contamination of the ligands used is within the desired range.

The chloride content can be determined analytically in a simple manner, for example by aqueous titration. A more extensive determination is that of the total chlorine content, which, as well as the chlorides, also encompasses chlorine bound in other forms. Emphasis on the total chlorine content is also of material relevance, in that it cannot be ruled out that chlorine bound in another form is also able to damage the reactor. In judging the limits for total chlorine, however, the chloride fraction remains crucial.

A suitable method for determining the total chlorine content is the combustion according to Wickbold with sample preparation to DIN 51408 and analysis by ion chromatography to DIN EN ISO 10304.

The patent literature discloses various methods for reducing the total chlorine content of organophosphorus ligands after the actual synthesis:

EP 0 285 136 claims a process for purifying tertiary organophosphites of pentavalent organophosphorus compounds which form as by-products of the synthesis or else as degradation or hydrolysis products of the tertiary organophosphites. The process envisages the treatment of the dissolved contaminated organophosphite with water at elevated temperature in the presence of a Lewis base. Lewis bases used are inorganic salts (carbonates, hydroxides, oxides), tertiary amines and polymers which carry amine groups.

One disadvantage of this process lies in the treatment with water. Not only the contaminants to be removed but also the tertiary organophosphites themselves react under the conditions specified, such that a portion of the product of value is lost according to the hydrolysis stability of the organophosphites.

DE 10 2004 049 339 describes a process for purifying phosphorus-containing chelate ligands by means of extraction using a polar extractant. The crude ligand was extracted here six times with a polar solvent, and then has a content of amine base, amine hydrochloride or mixtures thereof of less than 100 ppm. In this type of purification, however, enormous amounts of solvent are needed, which is in need of improvement from an economic and ecological point of view.

CN 101684130 A discloses the purification of phosphite ligands through the addition of deionized water and subsequent extraction. The organic solvent is removed by distillation in a subsequent step, and the crude product is recrystallized again. In this way, it was possible to obtain a product having a residual chlorine content of 0.01% by weight of chlorine.

In order to reduce the chlorine content of the ligand by this method, an extraction and a subsequent recrystallization are thus necessary. This means that a large amount of solvent has to be used, and yield losses because of the various purification steps and the possible lack of hydrolysis stability of the organophosphites cause a portion of the product of value to be lost.

WO 2012 095253 describes a process for preparing 6,6'-[(3,3'-di-tert-butyl-5,5'-dimethoxy-1,1'-biphenyl-2,2'diyl)bis(oxy)]bis(dibenzo[d,f][1,3,2]dioxaphosphepin) (termed: "biphephos"). The purification of the ligand takes place by repeated washing with various solvents.

Besides washing, distillation and recrystallization, in the course of the preparation of organophosphorus compounds there is also the option to purify the contaminated organophosphorus product with the help of filtration:

For example, EP2091958B1 describes the preparation of bisphosphites which are obtained dissolved in toluene and are filtered. This results merely in a partial removal of the chlorine, which is in need of improvement with regard to the intended use of the prepared organophosphorus compound as ligand in the hydroformylation of olefins.

It is known from EP1097936B1 to purify an organophosphorus product intended as stabilizer and dissolved in an organic solvent by adding water, a base and a solid drying agent to the solution in order to dry the organic phase. This produces two layers, namely one aqueous layer and one organic layer. The two layers are separated, the drying agent is filtered off from the organic phase and the solvent is evaporated. The chlorine-containing contaminants are thus eliminated via the aqueous phase. The disadvantage of this process is considered to be the addition of the water since the separation off of the aqueous phase in production on an industrial scale will not be possible with the required purity, meaning that residual water is left in the purified product. There, it is capable of decomposing the just obtained organophosphorus compound again by hydrolysis. Particularly then, if the organophosphorus product is intended for use as ligand in catalyst complexes, the presence of water is to be declined with regard to the hydrolysis.

Good chlorine values can be achieved by combining several purification steps: A combination of filtration and recrystallization for the purification of biphephos is shown in WO 2012/095255A1. In this process, a solid organophosphorus product is slurried in a solvent and filtered by means of a frit. The resulting, again solid organophosphorus product comprised, besides the desired biphephos, 2500 ppm of total chlorine. In order to reduce the total chlorine content, the solid was suspended in a solvent, heated and filtered. Then, the filtrate was recrystallized. The resulting purified organophosphorus product had a total chlorine content of only 35 ppm.

Although such a chlorine content is entirely satisfactory, this purification process requires many processing steps and large amounts of different solvents for the recrystallization, meaning that it is more suitable for the laboratory scale than for industrial ligand synthesis.

SUMMARY

Proceeding from this prior art, the invention is based on the object of indicating an industrially practicable purification method in which the chlorine content of an organophosphorus product which comprises at least one organophosphorus compound and at least one chlorine compound as contaminant, can be reduced from originally 1000 to 100,000 ppm to a total chlorine content between 10 ppm and 10,000 ppm. The desired chlorine contents here are understood as total chlorine content, i.e. both organically bonded chlorine and inorganically bonded chlorine. The unit ppm stands for $10^{-6}$ and refers to the respective weights.

Furthermore, the purification process should dispense with the use of water on account of the hydrolysis stability of the organophosphites. Finally, for reasons of environmental protection, the use of large amounts of solvent—as are required for extraction or recrystallization—should be dispensed with.

Furthermore, it would be desirable to indicate a process which can be used universally for different ligand classes. This leads to a better automatability of the ligand synthesis and thus to a higher product quality. This is advantageous particularly for industrial syntheses and process developments since the same equipment can be used and it is possible to dispense with expensive investments in new plants. The number of necessary processing steps should also be kept as small as possible in order to reduce the susceptibility to error and the production time.

DETAILED DESCRIPTION

These objects are achieved by a process of the genus specified at the start having the steps:
a) provision of the contaminated organophosphorus product;
b) complete dissolution of the contaminated organophosphorus product in a solvent to give a contaminated solution;
c) separation of the contaminated solution by means of a filter and/or by means of a membrane separation unit to give a purified solution;
d) removal of the solvent from the purified solution to give a purified organophosphorus product.

The invention therefore provides a process for the purification of a contaminated organophosphorus product which comprises at least one organophosphorus compound and, as contaminant, at least one chlorine compound, having the steps a) to d).

The purification according to the invention takes place by means of a membrane and/or by means of a filter. Here, it is also possible to combine several membrane separation steps or filtration steps. Moreover, both filtration steps and membrane separation steps can be carried out.

The purification process makes do without water and without undue consumption of solvents. Nevertheless, the solvent constitutes an important element of the invention, since the contaminated organophosphorus compound has to be completely dissolved in the solvent before the purification by means of filter and/or membrane separation unit.

The complete dissolution of the organophosphorus product is an essential distinguishing feature of the present invention compared to other filtration processes, such as for example the processes known from EP2091958B1 or WO 2012/095255A1:

A "complete dissolution" of the contaminated organophosphorus product is to be understood as meaning that both the desired organophosphorus compound and the undesired chlorine compounds are dissolved in their entirety in the solvent. Consequently, solid must no longer be visible in the solution. The visual test suffices for the success desired according to the invention. Of course, residual particles can still be detected in an optically complete solution with suitable, objective measurement methods. However, the process according to the invention should also be able to be practised easily. Consequently, a visual test is considered to be a satisfactory criterion for the assessment of a complete solution in the context of the invention.

The solvent-based filtration processes known in the prior art, by contrast, do not operate with a complete dissolution of the contaminated organophosphorus product; rather, it is customary in ligand synthesis to provide the organophosphorus compound as a suspension or slurry in the solvent and then to filter it. Thus, the amount of toluene used in the synthesis of structure D-1 in EP2091958B1 does not suffice to completely dissolve the substance D-1 therein. WO 2012/095255A1 explicitly discusses suspending or slurrying, but not a complete, solid-free solution.

The complete dissolution of the contaminated organophosphorus product including the chlorine soiling in the solvent permits a more selective separation of the organophosphorus compound from the chlorine compound on the filter or on the membrane. In the separation step c) a purified solution is produced from which the chlorine compound is depleted. After removing the solvent from the purified solution—this is effected in a manner known per se such as e.g. by distillation—a purified organophosphorus product is obtained whose total chlorine content is significantly lower than that of the originally provided, contaminated organophosphorus product. The removed solvent can be recycled and be used again for dissolving contaminated organophosphorus product. The disposal expenditure for the solvent drops as a result.

As already mentioned, the synthesis of some organophosphorus compounds takes place in a suspension or a slurry. It makes little sense to isolate the organophosphorus product from the suspension or from the slurry and then to dissolve it again in the solvent. Particularly when the synthesis of the organophosphorus product and its purification takes place at the same site and/or even in the same apparatus, it makes more sense to carry out the two steps a) provision of the contaminated organophosphorus product;
and
b) complete dissolution of the contaminated organophosphorus product in a solvent to give a contaminated solution;

together in one operation in which the contaminated organophosphorus product is provided completely dissolved in the contaminated solution.

The two steps a) and b) then take place at practically the same time. If the synthesis of the organophosphorus product takes place in suspension, i.e. in the case of incompletely dissolved organophosphorus product, the complete dissolution can inter alia be achieved by adding further solvent or increasing the temperature.

The provision of a contaminated organophosphorus product in solid form (i.e. amorphous or crystalline) then makes sense if the solvent used for the purpose of purification is a different solvent to the one used during the synthesis of the organophosphorus product.

The purification process according to the invention serves to free the contaminated organophosphorus product from its chlorine-containing contaminants. The separation off of the chlorine compounds takes place following complete dissolution of the contaminated organophosphorus product with all of its contaminants in the solvent. It therefore goes without saying that the total chlorine content of the purified solution is lower than that of the total chlorine content of the contaminated solution. The contaminated solution is accordingly purified of the chlorine compounds dissolved therein. As a result, the purified solution is obtained. In parallel to this, a more heavily contaminated solution is obtained in which the undesired contaminants are enriched. The total chlorine content of the more contaminated solution is accordingly greater than the total chlorine content of the contaminated solution.

The process according to the invention makes it possible to reduce the total chlorine content of a contaminated organophosphorus product, which is between 1000 and 100,000 ppm, in the purified state to a value between 10 and 10,000 ppm. Preferably, the purification process leads to a total chlorine content of the purified organophosphorus product between 10 and 1000 ppm. The unit ppm stands here for one millionth of a weight fraction. The total chlorine content includes both organic and inorganic species. A suitable method for determining the total chlorine content is the combustion according to Wickbold with sample preparation to DIN 51408 and analysis by ion chromatography to DIN EN ISO 10304.

This is because the contaminated organophosphorus product can contain organic chlorides and/or inorganic chlorides. Organic chlorides contain at least one carbon atom, whereas inorganic chlorides do not include any carbon. Contamination of the organophosphorus product by the following chlorides is particularly likely, since these chlorine compounds are either required in the course of synthesis of organophosphorus compounds or are unavoidably produced as by-products:

phosphorus trichloride, chlorophosphites, dichlorophosphites, hydrochlorides of amines, hydrochlorides of alkali metals, chlorides of alkaline earth metals, chlorine-containing acids obtainable from the hydrolysis of phosphorus trichloride.

Therefore, the contaminated organophosphorus product preferably has at least one of the listed chlorides.

The solvent selected is a substance which is able to dissolve both the organophosphorus compound as well as the chlorine-containing contaminant. Otherwise, a complete dissolution of the contaminated organophosphorus product therein would not be possible. Solvents that can be used are either a pure substance from the list below, or else a mixture of two or more substances from this group:
- aromatic hydrocarbons such as in particular toluene, xylene, o-xylene, cresol;
- ethers, such as in particular tetrahydrofuran (THF), petroleum ether, diethyl ether, methyl tert-butyl ether (MTBE);
- nitriles such as in particular acetonitrile (ACN);
- ethyl acetate;
- acetone;
- alcohols such as in particular methanol, ethanol, isopropanol, butanol.

The just mentioned solvents are organic solvents. The contaminated solution, i.e. the contaminated organophosphorus product completely dissolved in the organic solvent, consequently forms an organic phase. Since the process is preferably carried out in the absence of water on account of the susceptibility to hydrolysis of the organophosphorus products, no aqueous phase is formed alongside the organic phase. On account of the complete dissolution, the contaminated solution is solid-free. The organic phase formed by the contaminated solution is therefore the single phase in the system formed from organophosphorus product, contaminant and solvent.

Depending on the solvent and in particular the organophosphorus compound, a complete dissolution of the contaminated organophosphorus product at room temperature is not always possible. For this reason, a preferred development of the invention envisages dissolving the contaminated organophosphorus product at elevated temperature. The temperature here should be selected such that the solvent still does not start to boil. The temperature of the solvent used should therefore be between 20° C. and the boiling temperature of the selected solvent. Optimally, the temperature range is from 40° C. to 120° C. The increase in the temperature of the solvent also makes it possible to reduce the amount of solvent. This is particularly advantageous if a solvent that is harmful to health, environmentally impactful or simply expensive is used.

In one embodiment variant of the invention, the separation of the contaminated solution takes place by means of a filter. A filter separates predominantly mechanically according to the sieve effect, i.e. selectively according to the particle size. In some filtration methods, adsorption effects also play a role. The undesired chlorine compounds are unable to pass through the filter and therefore accumulate on this side of the filter in the filter cake. On the other side of the filter, in the filtrate, the chlorine-containing contaminants are depleted. Therefore, the purified solution is produced behind the filter as filtrate.

Suitable filters are both surface filters and also deep-bed filters. It is possible to use frits, filter candles, filter bags or filter cloths. The filters can be produced from ceramic or from plastics such as polypropylene.

The basic knowledge of the person skilled in the art in the field of filtration is evidenced by the following literature:
Pongratz et al., Handbuch der industriellen Fest-/Flüssigfiltration [Handbook of industrial solid/liquid filtration] (2000);
Sparks, Trevor: Solid-Liquid Filtration—A Users' Guide to Minimizing Costs and Environmental Impact; Maximizing Quality and Productivity. Elsevier (2012);
Cheremisinoff, Nicholas P.: Liquid Filtration (2nd Edition). Elsevier (1998)
Sutherland: Filters and Filtration Handbook (2008).

A particularly preferred embodiment of the filtration variant envisages that the separation of the contaminated solution is carried out in the presence of a filtration auxiliary. The filtration auxiliary is added to the solvent for this purpose either directly before the filtration of the contaminated solution or even earlier. Filtration aids bind the contaminants to be separated off in part physically and thereby prevent the filter being overcome. As a rule, the particles to be separated off form a layer on the filter surface and form bridges via the pores in the filter. Only these bridges in most cases bring about a complete separation of the particles. At the start there is therefore usually also leakage of the particles. The partial filtration with filter auxiliaries here has the advantage of building up these bridges already with the filter auxiliary and of preventing leakage of the particles from the product mixture.

Filtration aids used may be either mineral filtration aids, for example silicon dioxide, or organic filtration aids, for example cellulose or activated carbon. It is also possible to mix different filtration aids.

In a second variant of the invention, the separation of the contaminated solution takes place by means of a membrane separation unit. In contrast to a filtering, the membrane separation is based not only on the sieve effect, but moreover also on dissolution and diffusion effects. A further difference compared to filtration is that the substances to be separated off by means of membrane technology can completely overcome the membrane; however, this only at a reduced rate. The selective separation in practice in most cases additionally requires the establishment of corresponding overflow rates. A membrane separation also presupposes a clear pressure gradient between both sides of the membrane, the so-called transmembrane pressure, whereas in the case of filtration the pressure loss is considerably less. However, a transmembrane pressure is not always inevitably required, for example if the driving force results from a unbalanced dissolution equilibrium (reverse osmosis). A membrane separation is consequently significantly more complex and technically demanding than a filtration. Nevertheless, it allows the removal of contaminants which cannot be removed in the course of a classic filtration.

An introduction to membrane technology is given by:
Melin/Rautenbach: Membranverfahren. Grundlagen der Modul—and Anlagenauslegung. [Membrane Processes. Fundamentals of Module and System Design] Springer, Berlin Heidelberg 2004.

It has been found that chlorine compounds permeate the membrane particularly well. For this reason, during the membrane separation of the contaminated solution, the purified solution is thus produced as retentate in front of the membrane. Here too, an essential difference is found compared to a filtration, where the contamination is retained by the filter. Retentate is the term used in membrane technology to refer to the material stream from a membrane separation unit which, from the view of the inflowing feed, is drawn off in front of the membrane. The material stream which is drawn off behind the membrane is referred to as permeate since it has overcome the membrane. As regards the terminology used in membrane separation technology, reference is made to Melin/Rautenbach.

An important criterion for success when applying membrane technology is the choice of membrane material suited to the separation task. On account of the complex interaction between membrane and the materials to be separated, the identification of the membrane material is anything but trivial. Added to this is the fact that the membrane must be stable to the solvent used. Silicone-based polymers or polyethersulfone have proven particularly suitable as separation-active membrane materials for the purification of the chlorine-contaminated organophosphorus product since they have a significantly higher permeability for the typical chlorides than for organophosphorus compounds. Polyimide is likewise suitable.

The membrane separation unit can contain a multiplicity of membrane modules which can be connected to one another in different ways. The customary module connections are contemplated here, as for example Melin/Rautenbach describe. The membrane modules themselves can be configured constructively in different variants, for example as pocket modules, plate modules, coil modules, hollow fibre modules, capillary modules or hose modules.

Besides the construction, process parameters of the membrane separation also have an influence on the separation result. Important operating parameters are the selected solvent, the transmembrane pressure and the overflow rate. The membrane technologist knows how to suitably select these operating parameters.

Of particular importance is the separation temperature, i.e. the temperature at which the contaminated solution is placed on the membrane. This is because the permeability of many membrane materials is dependent on the temperature. Since the temperature of the solvent during the dissolution of the contaminated organophosphorus product is likewise attributed major significance, a preferred development of the invention envisages that the membrane separation takes place at a temperature which deviates from the temperature during the complete dissolution of the contaminated organophosphorus product with solvent. Accordingly, between step b) and step c) either a deliberate heating or a deliberate cooling of the contaminated solvent takes place. Whether cooling or heating specifically has to be carried out depends on the solvent used, the organophosphorus compounds and chlorides dissolved therein, and also the separation-active membrane material. As a rule, the separation of the contaminated solution by means of the membrane separation unit will take place at a temperature of 10 to 80° C., particularly preferably 20 to 60° C.

As explained at the start, there is a large number of technically relevant organophosphorus compounds which are used for the most diverse of purposes. Freedom from chlorine can therefore be a greater or lesser priority for different intended uses of the various organophosphorus compounds. Particularly high requirements are placed on the total chlorine content of organophosphorus products wherever the actual organophosphorus compound is used as ligand in a homogeneously catalysed, continuously operated reaction whose reaction apparatuses are damaged by chlorides.

Organophosphorus compounds which are typically used as ligands in homogeneous catalyst systems are phosphines, diphosphines, phosphonites, phosphinites, phosphoramidites, monophosphites and bisphosphites. The purification process according to the invention is therefore used in particular in connection with the synthesis of these classes of substance.

Particularly preferably, it serves for the purification of organophosphorus products which comprise phosphoramidites or phosphites. It is in particular intended for purifying bisphosphites, it being particularly suitable for the purification of the bisphosphites of the structural formulae (I) to (IV):

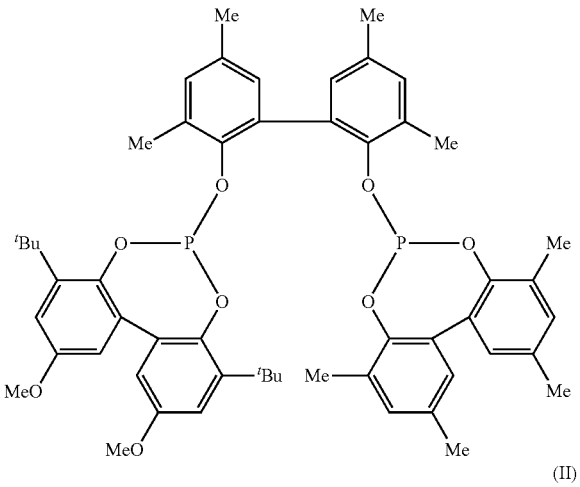

(I)

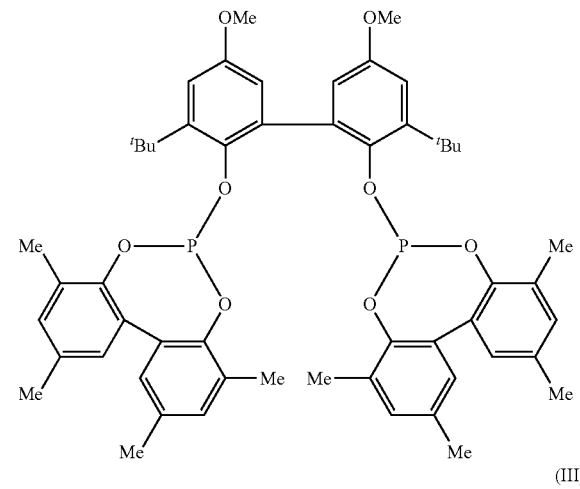

(II)

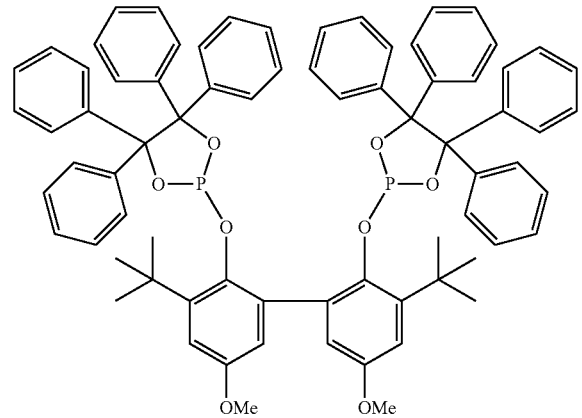

(III)

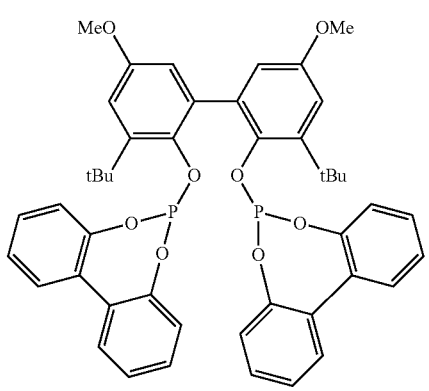

(IV)

On account of the particular suitability of the described process for the purification of organophosphorus products produced during ligand synthesis, a process for producing a catalyst system comprising a metal and at least one organophosphorus compound as ligand is likewise provided by the invention, provided that in the production of the catalyst system an organophosphorus product purified according to the invention is used which comprises those organophosphorus compounds which are typically used as ligand in catalyst systems.

The production of the catalyst system takes place in most cases not at the site at which the ligand synthesis also takes place, but in situ, i.e. where the catalyst system is used, namely in the reactor. The catalyst system is produced here by introducing the organophosphorus product produced ex situ and purified according to the invention into the reactor together with the metal. The actual catalyst system is formed only in the reactor in the presence of the reactants.

Since the high purity of the organophosphorus product achieved thanks to the process according to the invention develops its advantages ultimately only at the site of use of the organophosphorus product, the implementation of reactions in reactors which react particularly sensitively to the removed chlorides is likewise provided by the invention, specifically when unsaturated compounds are hydroformylated or hydrocyanated or hydrogenated in the presence of a homogeneous catalyst system, provided the catalyst system has a metal and at least one organophosphorus compound as ligand, and provided during the production of the catalyst system the corresponding organophosphorus product has been purified according to the invention. Particularly at risk are reactors made of steel, meaning that the purification process is in particular then advantageously used if the catalysed reaction takes place in a steel apparatus.

EXAMPLES

The purification according to the invention of chlorine-contaminated organophosphorus compounds will now be explained by reference to some working examples. The following abbreviations are used here:
ACN=acetonitrile
CPG=core-pulled precision glass
DM water=demineralized water
EtOAc=ethyl acetate
acac=acetylacetonate
NEt$_3$=triethylamine
DMAB=dimethylaminobutane
KO$^t$Bu=potassium tert-butylate
RT=room temperature All the preparations which follow were carried out under protective gas using standard Schlenk techniques. The solvents were dried over suitable desiccants before use (Purification of Laboratory Chemicals, W. L. F. Armarego (Author), Christina Chai (Author), Butterworth Heinemann (Elsevier), 6th edition, Oxford 2009).

The products were characterized by means of NMR spectroscopy. Chemical shifts (δ) are reported in ppm. The $^{31}$P NMR signals were referenced according to: $SR_{31P}=SR_{1H}*(BF_{31P}/BF_{1H})=SR_{1H}*0.4048$. (Robin K. Harris, Edwin D. Becker, Sonia M. Cabral de Menezes, Robin Goodfellow, and Pierre Granger, Pure Appl. Chem., 2001, 73, 1795-1818; Robin K. Harris, Edwin D. Becker, Sonia M. Cabral de Menezes, Pierre Granger, Roy E. Hoffman and Kurt W. Zilm, Pure Appl. Chem., 2008, 80, 59-84). The chlorine determination was effected in the form of combustion according to Wickbold; with sample preparation to DIN 51408 and analysis by ion chromatography to DIN EN ISO 10304.

Preparation of the Ligand (III)

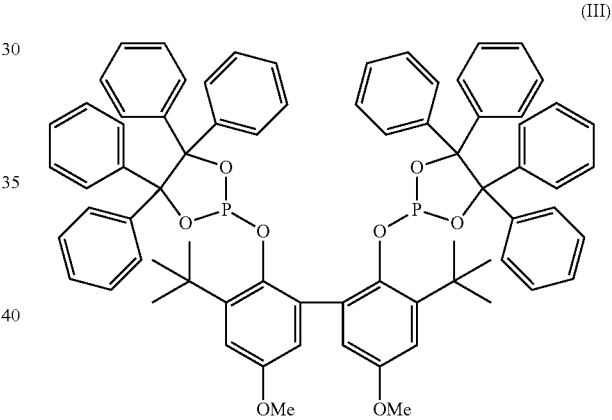

(III)

The synthesis of the bisphosphite ligand (III) was carried out analogously to the instructions in DE 102006058682. However, the base used was KOtBu (potassium tert-butylate).

In a 2000 ml Schlenk flask, 53.0 g (0.122 mol) of 1-chloro-3,3,4,4-tetraphenylphospholane (chlorophosphite) were introduced and dissolved in 800 ml of dried acetonitrile and stirred for two hours. In a second secured Schlenk flask (1000 ml), 15.8 g (0.043 mol) of 3,3'-di-tert-butyl-5,5'-dimethoxy-[1,1'-biphenyl]-2,2'-diol and 13.9 g (0.123 mol) of potassium tert-butylate were weighed out and 800 ml of dried acetonitrile were added. Then, this slurry was added dropwise at RT with stirring over a period of 3.5 h to the "chlorophosphite" solution and stirred overnight at RT.

For the work-up, the resulting solid was filtered and washed four times with 200 ml of degassed ACN. The remaining solvent was removed at $10^{-1}$ mbar for 3 h at 40° C. under reduced pressure and 43.9 g (88%) of the crude ligand (III) were obtained.

$^{31}$P{$^1$H}-NMR (C$_6$D$_6$, 202 MHz): δ=145.62 ppm. $^1$H-NMR (500 MHz, C$_6$D$_6$): δ=1.39 (s, 18H), 3.32 (s, 6H), 6.84-6.88 (m, 7H), 6.89-6.94 (m, 7H), 6.95-7.00 (m, 4H), 7.04-7.09 (m, 8H), 7.21-7.30 (m, 10H), 7.57 (d, J=7.5 Hz, 4H), 7.65 (d, J=7.5 Hz, 4H) ppm. Elemental analysis (calc. for $C_{74}H_{68}O_8P_2$=1147.29 g/mol): C, 77.00 (77.47); H, 5.66 (5.97); P, 5.82 (5.40) %.

Purification of the Ligand (III)

27.1 g of the crude ligand (III) were dissolved in 1900 ml of degassed toluene overnight at RT (Cl value according to Wickbold of the crude ligand (III): 7.5% by weight). The batch is transferred to a nitrogen-flushed 2-liter pressure filtration device with a filter area of 130 cm² and separated through ultrafiltration membrane from Microdyn Nadir of the type UV150T. Ultrafiltration is a type of membrane process, although the name may suggest otherwise. The separation temperature was 20° C. and the transmembrane pressure was 0.4 bar. The average permeate flow during the entire membrane separation was 57 ml/min.

The retentate produced had a chlorine value, determined according to Wickbold, of 55 mg/kg.

The chlorine value was thus able to be reduced for a ligand yield of 81.2% by 99.9%.

Preparation of the Ligand (I)

The organophosphorus compound 4,8-di-tert-butyl-2,10-dimethoxy-6-((3,3',5,5'-tetramethyl-2'-((2,4,8,10-tetramethyldibenzo[d,f][1,3,2]dioxaphosphepin-6-yl)oxy)-[1,1'-biphenyl]-2-yl)oxy)dibenzo[d,f][1,3,2]dioxaphosphepine, with the structural formula (I)

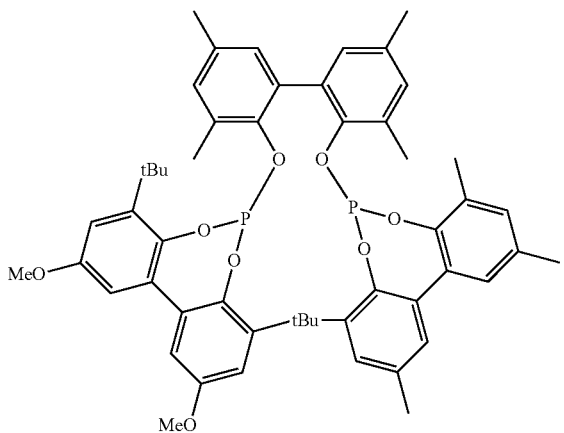

is referred to here as ligand (I). The synthesis of this ligand was carried out according to the instructions in the German patent applications 102013219506.0 and 102013219508.7 which were still unpublished at the time of the application:

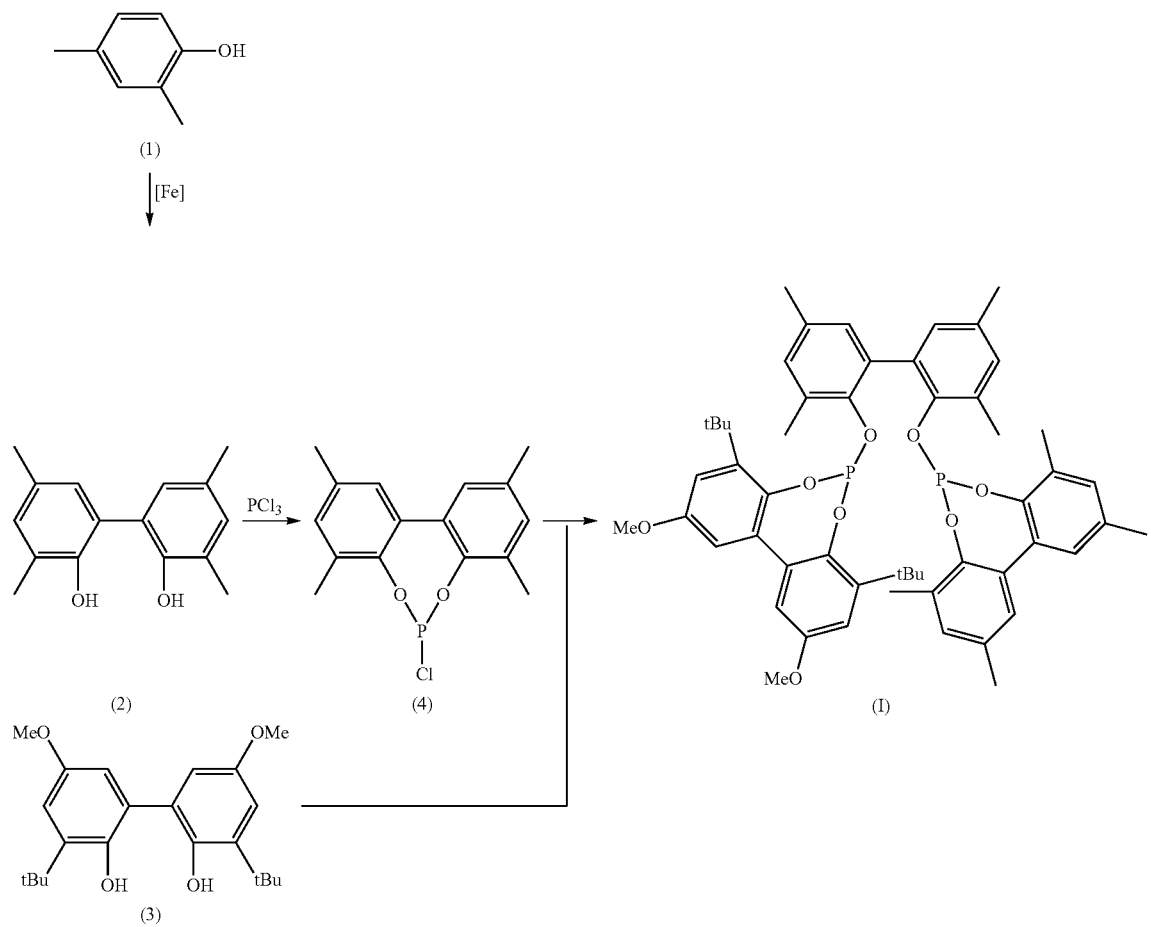

Synthesis of 2,2'-bis(3,5-dimethylphenol) (2)

The biphenol (2) used as a precursor was prepared by the following synthesis method.

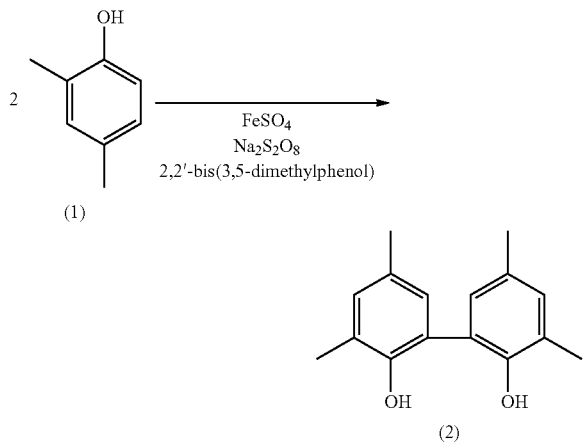

In a 500 ml Schlenk with CPG stirrer, intermediate section and glass stirrer, 1.42 g (0.005 mol) of iron(II) sulphate heptahydrate and 12.35 g (0.1 mol) of 2,4-dimethylphenol in 150 ml of DM water and 5 ml of cyclohexane were introduced and heated to 40° C.

In a 100 ml beaker, 25.36 g (0.146 mol) of sodium peroxodisulphate were dissolved in 80 ml of DM water. At the start of the reaction, a small portion of $Na_2S_2O_8$ solution was added to the phenol. Subsequently, a smaller portion of the solution was added every 10 min. After 30 min, the addition of $Na_2S_2O_8$ solution had ended.

After a reaction time of 5 h, 300 ml of cyclohexane and 200 ml of water were added to the reaction solution, which was stirred for 20 min, then transferred while warm to the separating funnel.

The organic phase was separated off and concentrated to dryness. The product (5) was obtained in 69% yield (10.6 g).

Synthesis of 2,2'-bis(3,5-dimethylphenol) chlorophosphite (4)

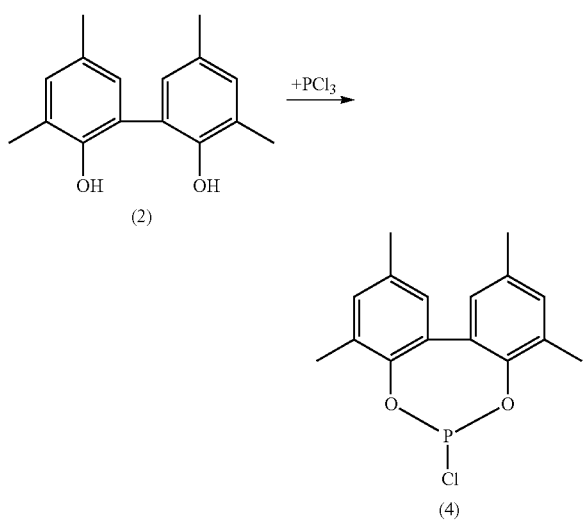

A secured 2 l Schlenk with magnetic stirrer was initially charged with 440 ml of phosphorus trichloride. 120 g of 2,2'-bis(3,5-dimethylphenol) were weighed into a second secured 1 l Schlenk and 500 ml of dried toluene were added with stirring. The biphenol-toluene suspension was metered into the phosphorus trichloride within 4 h at 63° C. After completion of the addition, the reaction mixture was stirred overnight at temperature. The next morning, the solution was concentrated while warm (45° C.) and the product was obtained in 96.5% yield (153 g). $^{31}$P NMR: 175.59 (94.8% 2,2'-bis(3,5-dimethylphenol) chlorophosphite), 4.4% various PC1 compounds, 0.8% P—H compound.

General Procedure for the Preparation of the Ligand (I):
Variant 1, in $ACN/NEt_3$:

In a 1000 ml Schlenk flask, under protective gas, 38.75 g (0.121 mol) of 2,2'-bis(3,5-dimethylphenyl) chlorophosphite were dissolved in 150 ml of degassed ACN and heated to 35° C. In a second Schlenk flask (500 ml), 20.1 g (0.056 mol) of 3,3'-di-tert-butyl-5,5'-dimethoxy-[1,1'-biphenyl]-2,2'-diol were dissolved in 150 ml of degassed ACN, and 40.9 ml of degassed triethylamine (0.29 mol) were added while stirring. Then the biphenol/triethylamine solution was slowly added dropwise to the chlorophosphite solution. After a post-reaction time of 1 h, the reaction solution was stirred overnight at 45° C.

Subsequently, the solution was filtered and the solid was washed three times with 100 ml of warm (45° C.) ACN. The crude product was obtained as a white solid (43.3 g, 86%). $^{31}$P NMR (202.4 MHz, toluene-$d_8$): 142.5 and 140.9 ppm. The chlorine content was later to be determined as 3.5% by weight.

Variant 2, in ACN/DMAB:

In a 100 ml Schlenk flask, under protective gas, 6 g (19.0 mmol) of 2,2'-bis(3,5-dimethylphenyl) chlorophosphite were dissolved in 20 ml of degassed ACN and heated to 35° C. In a second Schlenk flask (50 ml), 3.4 g (9.0 mmol) of 3,3'-di-tert-butyl-5,5'-dimethoxy-[1,1'-biphenyl]-2,2'-diol were dissolved in 15 ml of dimethylaminobutane (DMAB) and then slowly added dropwise to the chlorophosphite solution. The reaction was stirred at 35° C. overnight.

The next day, the solution was filtered and the solid was washed twice with ACN. The crude product was obtained as a white solid (5.3 g, 66%). $^{31}$P NMR (202.4 MHz, toluene-$d_8$): 142.8 and 141.2 ppm Variant 3, in $EtOAc/NEt_3$:

In a 100 ml Schlenk flask, under protective gas, 7.3 g (21.0 mmol) of 2,2'-bis(3,5-dimethylphenol) chlorophosphite were dissolved in 15 ml of degassed ethyl acetate and heated to 35° C. In a second Schlenk flask (100 ml), 3.9 g (9.5 mmol) of 3,3'-di-tert-butyl-5,5'-dimethoxy-[1,1'-biphenyl]-2,2'-diol were dissolved in 7.0 ml of $NEt_3$. Subsequently, the biphenol/triethylamine solution was slowly added dropwise to the chlorophosphite solution within 20 minutes. The solution was stirred at 35° C. for a further hour and then at 45° C. overnight.

This solid was suspended in degassed ACN at 75° C. for 1.5 h and separated off and after-washed with warm ACN. Subsequently, the product was suspended in dried toluene at 35° C. for 1.5 h and separated off.

The crude product was obtained as a white solid (5.0 g, 58%). $^{31}$P NMR (202.4 MHz, toluene-$d_8$): 142.5 and 140.9 ppm. The chlorine content was later to be determined as 4.5% by weight.

Purification of the Ligand (I) with the Help of Filtration and Membrane Separation:

95 g of the crude ligand (I), prepared according to variant 1, were dissolved in 1900 ml of toluene at 75° C. within 45 minutes (Cl value according to Wickbold of the crude ligand (I): 3.5% by weight) and transferred to a nitrogen-flushed 2-liter pressure filtration device with a filter area of 130 cm² and filtered through the filter cloth Propex 14K. The filtration temperature was 20° C. and the filtration pressure was 0.5 bar. The filtration time was 9 minutes.

The filtrate was again filtered under inert conditions through a filter bed from PALL of the type Seitz® K 100 with an area of 20 cm². A sample of the generated filtrate produced the following chlorine value, determined according to Wickbold: 820 mg/kg.

The remaining filtrate of 1550 g was finally separated in a stirred dead-end separating cell from Evonik Membrane Extraction Technology Limited of the type METCELL® with a nanofiltration membrane. An organophilic nanofiltration membrane from GMT Membrantechnik GmbH of the type ONF-2 was used. The membrane area is 54 cm². The active membrane area is installed facing the feed. The permeate flows away through the sintered metal plate of the separating cell via the permeate outlet. The membrane separation was carried out at 27° C. and a nitrogen pressure of 30 bar. 1137 g of permeate were produced. This corresponds to a volumetric concentration factor of 3.8.

The permeate produced comprises 8 g of solid and also a chlorine value according to Wickbold of 880 mg/kg and comprised in particular the chlorine-containing contaminants as main constituent.

The retentate produced comprises 38 g of solid and also a chlorine value according to Wickbold of 260 mg/kg.

The chlorine value was thus able to be reduced by 98%.
Purification of the Ligand (I), Prepared According to Variant 3 by Means of Membrane Technology and Filtration with SiO₂ Filter Aids:

92.1 g of the crude ligand (I), prepared according to variant 3, were dissolved in 1900 ml of toluene at 75° C. (Cl value according to Wickbold of the crude ligand (I): 4.5% by weight). The filtration aid Hyflo SuperCel, based for the greatest part on SiO₂, was dried at 80° C. for 14 hours in a drying cabinet. 20 g of dried Hyflo SuperCel were stirred into 400 ml of dried toluene for 2 hours and then transferred to a nitrogen-flushed 2-liter pressure filter device with a filter area of 130 cm² and partially filtered on an ultrafiltration membrane. The ultrafiltration membrane used was a membrane from Microdyn Nadir of the type UV150T. The separation temperature was 20° C. and the transmembrane pressure was 0.4 bar. Subsequently, the crude solution was transferred slowly and with nitrogen-blanketing to the pressure filter device and then filtered at 20° C. and 0.4 bar.

The Cl value of the filtrate produced was 190 mg/kg.

The chlorine value was thus able to be reduced for a ligand yield of 77.6% by more than 99%.
Purification of the Ligand (I), Prepared According to Variant 2 by Means of Filtration and Cellulose Filter Aid:

73.2 g of the crude ligand (I), prepared according to variant 2, were dissolved in 1500 ml of toluene at 75° C. overnight (Cl value according to Wickbold of the crude ligand: 1.0% by weight) and admixed with 10 g of the cellulose-based filter aid Vitacell LC200.

This crude solution already comprises the filter aid VITA-CEL® LC 200, consisting of cellulose. Crude solution was transferred to a nitrogen-flushed 2-liter pressure filtration device with a filter area of 130 cm² and filtered through the filter cloth Propex 14K. The filtration temperature was 20° C. and the filtration pressure was 2 bar.

The filtrate was again filtered under inert conditions through a filter bed from PALL of the type Seitz® K 100 with an area of 20 cm². The filtrate produced gave a chlorine value, determined by X-ray fluorescence analysis (XRFA), of 0.15% by weight.

The chlorine value was thus able to be reduced for a ligand yield of 88.2% by 85%.
Purification of the Ligand (I), Prepared According to Variant 1 by Means of a Filter Cloth and a Filter Candle:

96.9 g of the crude ligand (I), synthesized according to variant 1, were dissolved in 1900 ml of degassed toluene at 75° C. overnight (Cl value according to Wickbold of the crude ligand (I): 3.5% by weight). The filter aid DIACEL® 300, consisting of cellulose, was dried at 80° C. for 14 hours in a drying cabinet. 25 g of dried DIACEL® 300 were stirred into 500 ml of dried toluene for 2 hours and then transferred to a nitrogen-flushed 2-liter pressure filter device with a filter area of 130 cm² and partially filtered on a filter cloth. The filter cloth used was a Propex 14K made of polypropylene. The filtration temperature was 20° C. and the filtration pressure was 2 bar. Subsequently, the crude solution was transferred slowly and with nitrogen-blanketing to the pressure filter device and then filtered at 20° C. and 2 bar.

The filtrate was again filtered under inert conditions through a 1" filter candle from PALL of the type Profile® II with a separation limit of 0.3 μm. From the filtrate produced, the following chlorine value, ascertained with X-ray fluorescence analysis (XRFA), was determined: 0.26% by weight.

The remaining filtrate was finally separated in a 2 l pressure filter device through an ultrafiltration membrane from Microdyn Nadir of the type UV150T at 20° C. and 2 bar. The retentate produced revealed a chlorine value, determined with X-ray fluorescence analysis (XRFA), of 0.12% by weight.

The chlorine value was thus able to be reduced for a ligand yield of 63% by 96.6%.

Preparation of the Ligand (IV)

The organophosphorus compound 6,6'-[(3,3'-di-tert-butyl-5,5'-dimethoxy-1,1'-biphenyl-2,2'diyl)bis(oxy)]bis(dibenzo[d,f][1,3,2]dioxaphosphepine with the structural formula (IV)

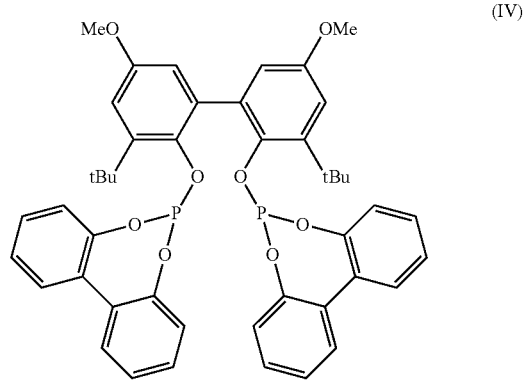 [SMILES: COc1cc(-c2cc(OC)cc(C(C)(C)C)c2Op2oc3ccccc3c3ccccc3o2)c(Op2oc3ccccc3c3ccccc3o2)c(C(C)(C)C)c1]

is also referred to as biphephos and hereinbelow as ligand (IV).

Its preparation was carried out analogously to WO 2012/095253 and WO 2012/095255 except that after-washing with solvent was carried out several times. As a result, the starting chlorine value was 180 ppm.

Membrane Purification of Ligand (IV):

30 g of the crude ligand (IV) (Cl value determined according to Wickbold of the crude ligand of 180 ppm) were dissolved in 1900 ml of toluene overnight at 70° C. The batch is transferred to a nitrogen-flushed 2-liter pressure filtration device with a filter area of 130 cm$^2$ and separated through ultrafiltration membrane from Microdyn Nadir of the type UV150T. The membrane temperature was 20° C. and the transmembrane pressure was 0.6 bar. The average permeate flow during the entire membrane purification was 15 ml/min.

The retentate had a chlorine value, determined according to Wickbold, of 30 mg/kg.

The chlorine value was thus able to be reduced for a ligand yield of 32.1 g by 83%.

Membrane Purification of Ligand (IV):

60.5 g of the crude ligand (IV) (Cl value determined according to Wickbold of the crude ligand of 180 ppm) were dissolved in 1900 ml of toluene overnight at 70° C. The batch is transferred to a nitrogen-flushed 2-liter pressure filtration device with a filter area of 130 cm$^2$ and separated through ultrafiltration membrane from Microdyn Nadir of the type UV150T. The membrane temperature was 20° C. and the transmembrane pressure was 0.6 bar. The average permeate flow during the entire membrane separation was 22 ml/min.

The retentate produced had a chlorine value, determined according to Wickbold, of less than 10 mg/kg.

The chlorine value was thus able to be reduced for a ligand yield of 64.4 g by 94%.

Purification of the Ligand (IV) by Means of a PP Filter Cloth in the Presence of Cellulose:

30 g of the crude ligand (IV) (Cl value determined according to Wickbold of the crude ligand of 180 ppm) were dissolved in 1900 ml of toluene overnight at 70° C. The filter aid DIACEL® 300, consisting of cellulose, was dried at 80° C. for 14 hours in a drying cabinet. 20 g of dried DIACEL® 300 were stirred into 500 ml of dried toluene for 2 hours and then transferred to a nitrogen-flushed 2-liter pressure filter device with a filter area of 130 cm$^2$ and partially filtered on a filter cloth. The filter cloth used was a Propex 14K made of polypropylene. The filtration temperature was 20° C. and the filtration pressure was 0.2 bar. Subsequently, the crude solution was transferred slowly and with nitrogen-blanketing to the pressure filter device and then filtered at 20° C. and 0.2 bar.

The filtrate was again filtered under inert conditions through a filter bed from PALL of the type Seitz® K 100 with an area of 20 cm$^2$. The retentate produced had a chlorine value, determined according to Wickbold, of 28 mg/kg.

The chlorine value was thus able to be reduced for a ligand yield of 31.2 g by 84%.

CONCLUSION

The experiments show that it is possible with the described purification methods to free contaminated organophosphorus products from chlorine compounds to a significant degree. The thus purified organophosphorus compounds can be used without reservation as ligands in industrially operated reactions, since corrosion of steel apparatuses is no longer to be feared on account of their low total chlorine content. The organophosphorus compounds under consideration themselves have proven their value as ligands in homogeneously catalysed hydroformylation.

Moreover, the purification processes described here can be automated easily and applied to all kinds of organophosphorus products. Consequently, it is predestined to being put into practice in the context of the industrial synthesis of organophosphorus compounds.

The invention claimed is:

1. A process for the purification of a contaminated organophosphorus product which comprises at least one organophosphorus compound and, as contaminant, at least one chlorine compound, having the following steps:
   a) providing the contaminated organophosphorus product;
   b) completing dissolution of the contaminated organophosphorus product in a solvent to give a contaminated solution;
   c) separating the contaminated solution by means of a filter and/or by means of a membrane separation unit to give a purified solution;
   d) removing the solvent from the purified solution to give a purified organophosphorus product.

2. The process according to claim 1, in which the steps
   a) providing the contaminated organophosphorus product; and
   b) completing dissolution of the contaminated organophosphorus product in a solvent to give a contaminated solution;
   take place in one operation by providing the contaminated organophosphorus product completely dissolved in the contaminated solution.

3. The process according to claim 1, wherein the total chlorine content of the purified solution is less than that of the total chlorine content of the contaminated solution.

4. The process according to claim 3, wherein the total chlorine content of the contaminated organophosphorus product is between 1000 ppm and 100,000 ppm, and that the total chlorine content of the purified organophosphorus product is between 10 ppm and 10,000 ppm where the unit ppm refers to the weight.

5. The process according to claim 1, wherein the contaminated organophosphorus product comprises at least one chlorine compound selected from the following group:
   organic chlorides comprising at least one carbon atom;
   inorganic chlorides without carbon atom;
   where particularly preferably at least one of the following chlorine compounds is present:
   phosphorus trichloride, chlorophosphites, dichlorophosphites, hydrochlorides of amines, hydrochlorides of alkali metals, chlorides of alkaline earth metals, chlorine-containing acids obtainable from the hydrolysis of phosphorus trichloride.

6. The process according to claim 1, wherein the solvent used is a substance selected from the following group, or that a mixture of several substances from this group is used as solvent:
   aromatic hydrocarbons such as in particular toluene, xylene, o-xylene, cresol;
   ethers, such as in particular tetrahydrofuran (THF), petroleum ether, diethyl ether, methyl tert-butyl ether (MTBE);
   nitriles such as in particular acetonitrile (ACN);
   ethyl acetate;
   acetone;
   alcohols such as in particular methanol, ethanol, isopropanol, butanol.

7. The process according to claim 6, wherein the contaminated solution forms a single organic phase, in particular, that alongside the organic phase, no aqueous phase is formed.

8. The process according to claim 1, wherein the complete dissolution of the contaminated organophosphorus product in the solvent takes place at a temperature above 20° C. and below the boiling temperature of the selected solvent.

9. The process according to claim 1, wherein the separation of the contaminated solution takes place by means of a filter, and that the purified solution is produced on the filter as filtrate with, if necessary, the separation of the contaminated solution being carried out in the presence of at least one filtration auxiliary, which has been added beforehand to the contaminated solution or the solvent.

10. The process according to claim 1, wherein the separation of the contaminated solution takes place by means of a membrane separation unit, and that the purified solution is produced as retentate of the membrane separation unit.

11. The Process according to claim 10, wherein the membrane separation unit has at least one membrane whose separation-active material is selected from the following membrane materials:
  silicone-based polymers
  polyethersulfone
  polyimide.

12. The process according to claim 10, wherein the separation of the contaminated solution takes place by means of the membrane separation unit at a temperature which deviates from the temperature during complete dissolution of the contaminated organophosphorus product in the solvent, in particular that the separation of the contaminated solution takes place by means of the membrane separation unit at a temperature of from 10° C. to 80° C.

13. The process according to claim 1, wherein the organophosphorus product comprises at least one organophosphorus compound selected from the following group:
  phosphines;
  diphosphines;
  phosphonites;
  phosphinites;
  preferably phosphoramidites;
  preferably monophosphites;
  particularly preferably bisphosphites, in particular one or more bisphosphites of the structural formulae (I) to (IV):

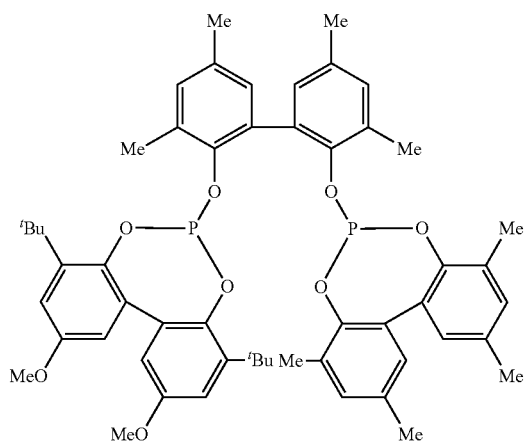

(I)

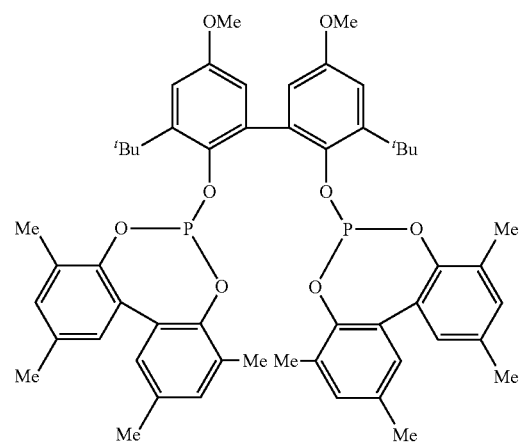

(II)

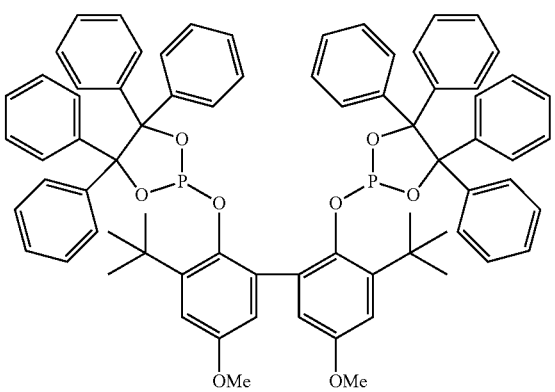

(III)

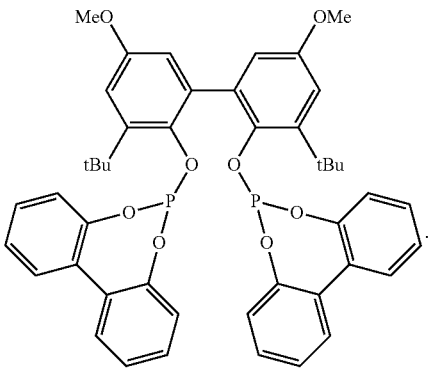

(IV)

14. The process for producing a catalyst system comprising a metal and at least one organophosphorus compound as ligand, wherein during the production of the catalyst system a purified organophosphorus product is used which has been obtained according to claim 13.

15. The process for the hydroformylation or for the hydrocyanation or for the hydrogenation of unsaturated compounds in the presence of a homogeneous catalyst system which has a metal and at least one organophosphorus compound as ligand, wherein the catalyst system has been produced according to claim 14.

* * * * *